(12) United States Patent
Lane (10) Patent No.: US 7,434,724 B2
(45) Date of Patent: Oct. 14, 2008

(54) DYNAMIC BARCODE FOR DISPLAYING MEDICAL DATA

(75) Inventor: John A. Lane, Weedsport, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 9 days.

(21) Appl. No.: 11/615,230

(22) Filed: Dec. 22, 2006

(65) Prior Publication Data

US 2008/0149701 A1    Jun. 26, 2008

(51) Int. Cl.
*G06F 17/00* (2006.01)
*G06K 7/10* (2006.01)

(52) U.S. Cl. .................. 235/375; 235/462.01

(58) Field of Classification Search ........... 235/375, 235/380, 439, 462.01
See application file for complete search history.

(56) References Cited

U.S. PATENT DOCUMENTS

| | | | |
|---|---|---|---|
| 4,835,372 A | 5/1989 | Gombrich |
| 4,857,716 A | 8/1989 | Gombrich |
| 5,036,852 A | 8/1991 | Leishman |
| 5,171,976 A | 12/1992 | Bone, Jr. |
| 5,270,522 A | 12/1993 | Bone, Jr. |
| 5,288,977 A | 2/1994 | Amendolia |
| 5,389,771 A | 2/1995 | Amendolia |
| 5,590,650 A | 1/1997 | Genova |
| 5,774,865 A | 6/1998 | Glynn |
| 5,805,152 A | 9/1998 | Furusawa |
| 5,939,699 A | 8/1999 | Perttunen |
| 5,954,641 A | 9/1999 | Kehr et al. |
| 6,082,620 A | 7/2000 | Bone, Jr. |
| 6,085,752 A | 7/2000 | Kehr et al. |
| 6,102,855 A | 8/2000 | Kehr et al. |
| 6,149,059 A | 11/2000 | Ackley |
| 6,620,104 B2 | 9/2003 | Tamura |
| 6,656,114 B1 | 12/2003 | Poulsen et al. |
| 6,666,377 B1 | 12/2003 | Harris |
| 6,755,795 B2 | 6/2004 | Marmaropoulos |
| 6,850,789 B2 | 2/2005 | Schweitzer, Jr. |
| 7,118,040 B2 | 10/2006 | Melick |
| 7,124,939 B2 | 10/2006 | Calaway |
| 7,188,767 B2 * | 3/2007 | Penuela et al. ............ 235/439 |
| 2004/0039255 A1 | 2/2004 | Simonsen et al. |
| 2005/0197621 A1 | 9/2005 | Poulsen et al. |
| 2006/0177795 A1 | 8/2006 | Sorensen et al. |
| 2007/0145137 A1* | 6/2007 | Mrowiec ............ 235/462.01 |

FOREIGN PATENT DOCUMENTS

EP    0 144 202 B1    5/1989
JP    2004181052 A  *  7/2004

OTHER PUBLICATIONS

International Searching Authority, International Search Report and Written Opinion in PCT No. PCT/US2007/087759, Mailed May 21, 2008.

* cited by examiner

*Primary Examiner*—Thien M Le
*Assistant Examiner*—April A Taylor
(74) *Attorney, Agent, or Firm*—Hishcock & Barclay, LLP (57) ABSTRACT

Disclosed in this specification is an apparatus and method for producing and displaying a dynamic barcode that permits authorized medical personnel to obtain confidential medical information while preventing unauthorized personnel from viewing the same. Any suitable dynamic medical information may be so displayed including blood pressure, temperature, respiration rate, heart rate, and the like.

21 Claims, 6 Drawing Sheets

DYNAMIC BARCODE FOR DISPLAYING MEDICAL DATA

FIELD OF THE INVENTION

This invention relates, in one embodiment, to a system for generating a dynamic barcode that comprises recent medical data concerning a patient. The dynamic barcode is updated as the medical condition of the patient changes. The present system provides for a method to display a patient's medical information without jeopardizing the patient's privacy.

BACKGROUND OF THE INVENTION

It has been a longstanding objective in the art to achieve a rapid and efficient method for recording and displaying dynamic medical data about a patient, while also protecting sensitive or confidential patient information. Such protection is mandated by the Health Insurance Portability and Accountability Act (HIPAA). One unexplored means for providing such protection includes the use of barcodes.

Barcodes are used to record and transmit large amounts of such data. Barcodes also allow data to be entered into a computer system, while greatly reducing the occurrence of human-related input error. Advantageously, barcodes are computer readable, but are not directly readable by humans. As such, the data contained in a barcode is somewhat encrypted. Unfortunately, once a barcode has been generated it is difficult to update without printing a fresh barcode (i.e. the barcode is static). Prior art barcodes are not generally adaptable to presenting dynamic data. A number of systems that utilize barcodes have been developed in the prior art, but to date, none has proven entirely satisfactory.

U.S. Pat. No. 4,835,372 (Patient Care System, issued May 30, 1989) and U.S. Pat. No. 4,857,716 (Patient Identification and Verification System and Method, issued Aug. 15, 1989) both to Gombrich et al., teach a tracking system that includes static barcodes disposed on the wrists of patients and their medication(s). Hospital employees can rapidly scan these barcodes to ensure the medications are properly associated with the correct patient. Unfortunately, the barcodes of Gombrich are static. Gombrich does not provide a method for communicating dynamic (i.e. frequently changing) data. Similar technology is disclosed in published PCT application WO1987/000659A1 to Clinicom Corporation (Patient Identification and Verification System and Method) and Japanese Patent Publication No. 02-027496 to Hitachi Medical Corporation (ID Information Writing/Reading Device).

U.S. Pat. No. 5,288,977 (System for Imprinting Patient-Identifying Barcodes onto Medical X-rays, issued Feb. 22, 1994) and U.S. Pat. No. 5,389,771 (Barcoding, issued Feb. 14, 1995), both to Amendolia et al., disclose a method for associating a patient's medical images with a barcode, thus helping to ensure the records are properly paired with the correct patient. Like Gombrich, the techniques of Amendolia can only track static data. A similar technique for tracking medicine bottles, rather than x-rays, is disclosed in U.S. Pat. No. 5,774,865 to Glynn (Patient Compliance and Monitoring System for Multiple Regimens using a Movable Bar Code Reader, issued Jun. 30, 1998).

U.S. Pat. No. 5,805,152 to Furusawa (Video Presentation System, issued Sep. 8, 1998) also discloses novel uses for barcodes. Furusawa discloses a system for interacting with video images by associating those displayed images with a barcode. The user can then interact with the video by selecting the appropriate barcode.

Unfortunately, the aforementioned prior art only provides means for communicating static data. It is substantially more difficult to reduce dynamic data to barcode format. Nevertheless, some dynamic barcodes have found limited uses in the prior art.

U.S. Pat. No. 5,270,522 (Dynamic Barcode Label System, issued Dec. 14, 1993) and U.S. Pat. No. 5,171,976 (Dynamic Coded Mechanical Metering System), both to Bone, disclose a method for converting a meter reading to a barcode format. As the meter reading changes, the barcode is updated with the changed value. An unskilled worker can record the current reading by simply scanning the barcode. The content of the aforementioned patents is hereby incorporated by reference into this specification.

U.S. Pat. No. 6,082,620 to Bone (Liquid Crystal Display, issued Jul. 4, 2000) also discloses a method for generating a dynamic barcode based upon input from an analog or digital device. The resulting dynamic barcode is displayed on a liquid crystal display (LCD). The content of the aforementioned patent is hereby incorporated by reference into this specification.

U.S. Pat. No. 5,939,699 to Perttunen et al. (Bar Code Display Apparatus, issued Aug. 17, 1999) teaches a method for generating a dynamic barcode in response to user input. The content of U.S. Pat. No. 5,939,699 is hereby incorporated by reference into this specification.

U.S. Pat. No. 6,666,377 to Harris (Bar Code Data Entry Device) provides an excellent discussion concerning the storage of large amounts of data within a barcode. Harris also provides an explanation of both one dimension and two dimensional (i.e. "matrix" or "Gettysburg Address") barcodes. U.S. Pat. No. 6,149,059 to Ackley (Bar Code Symbology Capable of Encoding Bytes, Words, 16-bit characters, etc. and Method and Apparatus for Printing and Reading Same) also provides excellent background information concerning barcode technology. The content of U.S. Pat. Nos. 6,666,377 and 6,149,059 is hereby incorporated by reference into this specification.

U.S. Pat. No. 7,118,040 to Melock et al. (Method and Apparatus for Bar Code Data Interchange) teaches methods for scanning barcodes that are displayed on a digital display, such as a computer monitor. The content of the aforementioned patent is hereby incorporated by reference into this specification.

Unfortunately, the prior art of record does not provide a method to quickly and easily record dynamic data from a medical sensors nor does the prior art provide a system to protect the privacy of the patient whose medical information is considered confidential under HIPAA.

Therefore, a medical device that generates and updates dynamic barcodes in response to input from a medical sensor is desired.

Further, a method for encoding dynamic medical data is desired, wherein the encoded dynamic data is generally protected from viewing by the public, but is available for viewing by authorized medical personnel.

SUMMARY OF THE INVENTION

The invention comprises, in one form thereof, a dynamic barcode that changes in response to input from a medical sensor.

In another form, the invention includes a method for displaying medical information about a patient that can be gathered by medical personnel without revealing the medical information to such personnel.

An advantage of the present invention is that the dynamic medical data can be gathered and displayed by an apparatus and method that limits the introduction of human error.

A further advantage of the present invention is that the dynamic medical data may be presented in a form that can be gathered, but not read, by medical personnel. The medical data can later be accessed by an authorized user.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
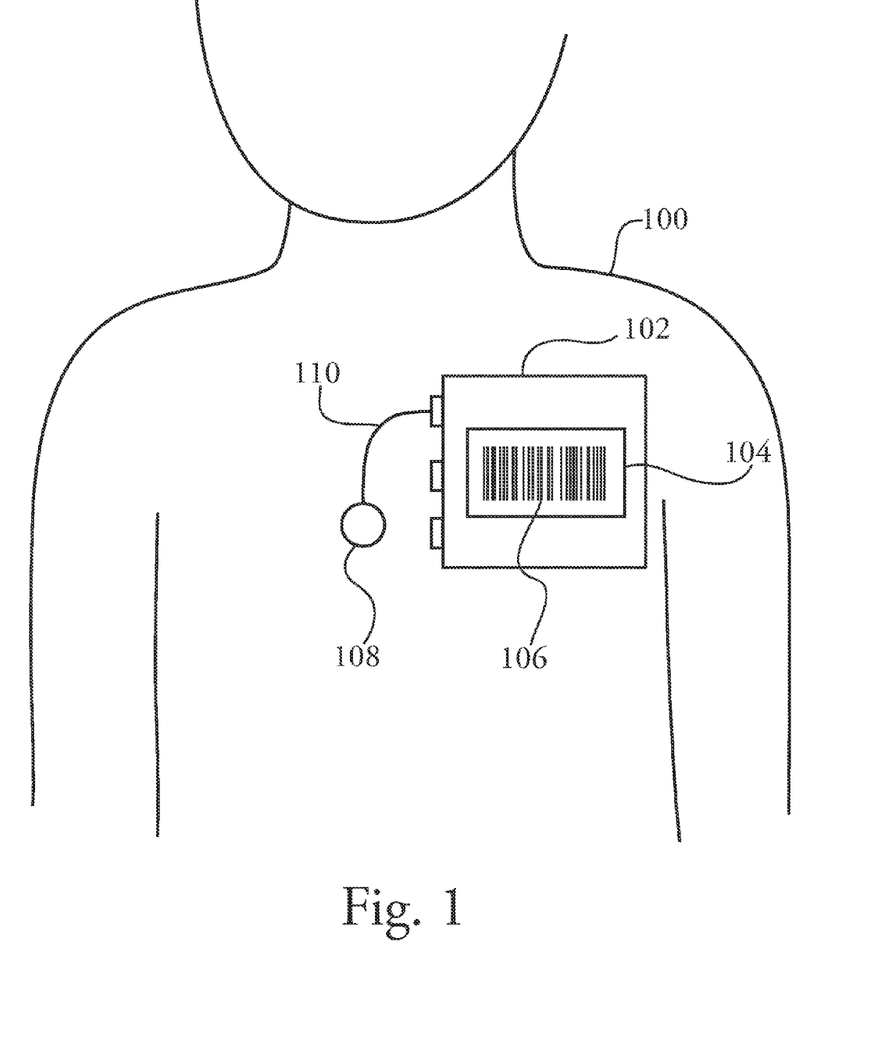
FIG. 1 is a schematic view of a medical device for use with the present invention.

Referring to FIG. 1, and the embodiment disclosed therein, patient 100 is wearing medical device 102. In the embodiment depicted in FIG. 1, medical device 102 is a badge configured to be worn by patient 100. In FIG. 1, medical device 102 is connected to medical sensor 108 via line 110. Medical sensor 108 may be, for example, a heart sensor, a temperature sensor, and the like. In another embodiment, the medical device 102 is a small, ambulatory device suitable for being disposed on the patient 100. For example, medical device 102 may be configured to be worn about the neck of patient 100. In another embodiment, medical device 102 is designed to be worn about the wrist of patient 100, or otherwise disposed on the patient's person. In yet another embodiment, the medical device 102 is designed to be disposed at the bedside of patient 100. Such an embodiment is particular useful in conjunction with medical sensors which are not ambulatory. Medical device 102, in turn, is comprised of digital display 104 (e.g. a LCD) and dynamic barcode 106 displayed thereon. Advantageously, barcode data is not human readable without the aid of a barcode scanner. As used in this specification, the term "human readable" is given the same meaning as defined and claimed in U.S. Pat. No. 6,082,620. Medical device 102 is configured to receive input from one or more medical sensors and thereafter generate dynamic barcode 106 that is representative of the input so received. Such an embodiment is illustrated in FIG. 2.

Figure 2:
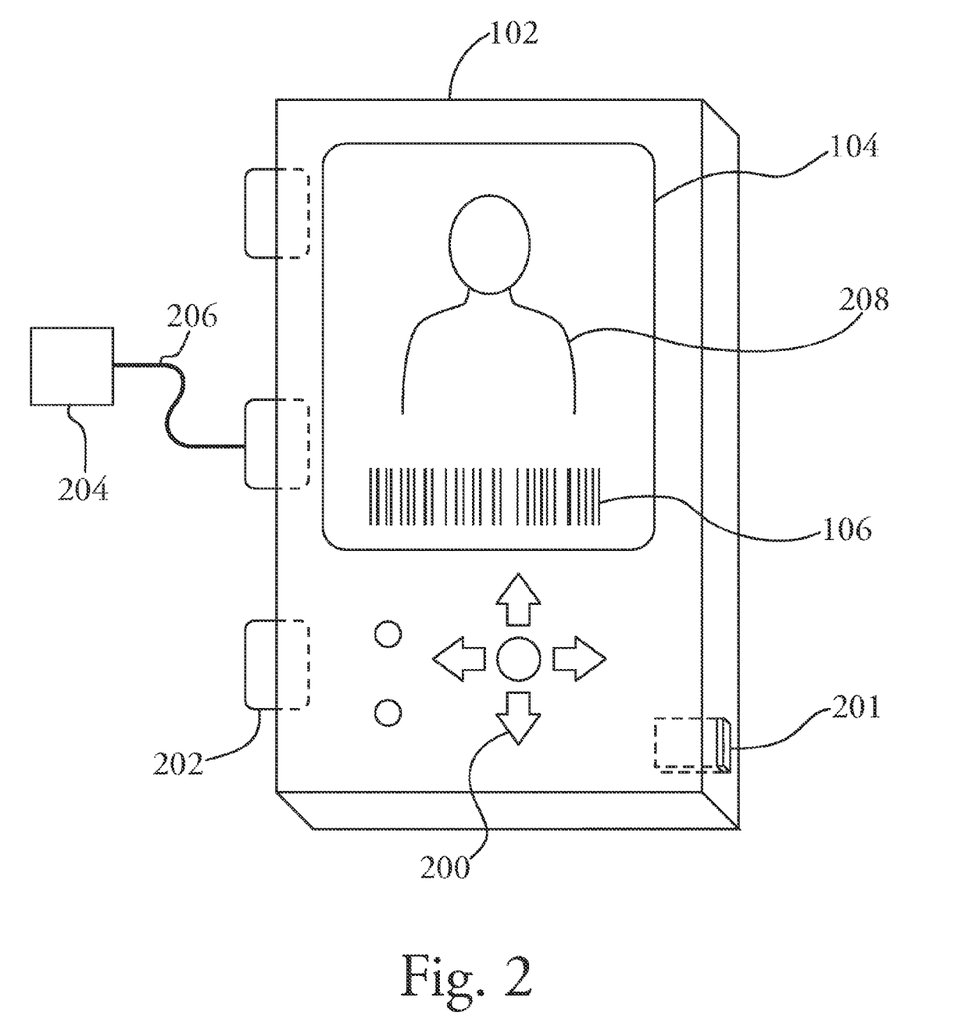
FIG. 2 is a more detailed schematic view of another medical device for use with the present invention.

FIG. 2 is a depiction of medical device 102 in greater detail. As shown in FIG. 2, medical device 102 is comprised of digital display 104 which displays dynamic barcode 106. Medical device 102 is further comprised of user input terminal 200, programming input terminal 201, and data input terminal 202. User input terminal 200, which is optional, may be any suitable means for a user to input data to medical device 102 manually. For example, in one embodiment, user input terminal 200 is a keyboard or other button input device. Programming input terminal 201 is any suitable means for connecting medical device 102 to a programmer (such as a computer) so that the programmer may program or reprogram medical device 102. In one embodiment, programming input terminal 201 is a universal serial bus (USB) port that permits medical device 102 to be connected to a programmer to receive programming instructions therefrom. Optionally, data can be downloaded from medical device 102 and stored in the programmer via programming terminal 201. Data input terminal 202 is any means for connecting medical device 102 to medical sensor 204 and receiving dynamic medical data from such medical sensor 204. Data input terminal 202 may be, for example, an electrical connection or a telemetric connection. In the embodiment depicted, medical device 102 is configured to connect to one or more medical sensor 204, although only one such medical sensor is so connected. Medical sensor 204 may be either an analog sensor (which provides an analog signal, such as a voltage range) or digital sensor (which provides a digital signal, such as a binary code).

In some embodiments of the invention, one or more alarms are operatively connected to the medical device 102. Such alarms are triggered when the dynamic medical data meets a certain predetermined criteria. For example, if the heart rate of the patient deviates outside of a predetermined threshold, then an alarm is triggered to notify the caregivers.

Referring again to FIG. 2, medical sensor 204 is any suitable medical sensor known in the art. By way of illustration, and not limitation, such a medical sensor 204 may be a heart sensor (such as an electrocardiogram (ECC) or pulse sensor), a respiration sensor, a blood pressure sensor, a temperature sensor, a blood oxygen level sensor, and the like. Any suitable medical sensor may find use in conjunction with the present invention. Examples of sensors include U.S. Pat. No. 6,850,789 (Combination SPO2/temperature measuring apparatus); U.S. Pat. No. 6,755,795 (Selectively Applied Wearable Medical Sensors); U.S. Pat. No. 6,620,104 (Vital Signal Detecting Apparatus and Noninvasive Blood Pressure Meter); U.S. Pat. No. 5,590,650 (Non-Invasive Medical Monitor System); U.S. Pat. No. 5,036,852 (Medical Equipment Monitor Apparatus and Method); and the like. The content of each of the aforementioned patents is hereby incorporated by reference into this specification. In the embodiment depicted in FIG. 2, medical device 102 is connected to medical sensor 204 via line 206. In another embodiment, the connection is a telemetric connection. In one such embodiment, the telemetric connection uses radio waves or infrared waves to facilitate the communication between medical device 102 and medical sensor 204. In yet another embodiment, not shown, the medical device 102 and the medical sensor 204 are unitary and the connection between the device and the sensor is disposed within a single housing. By way of illustration, and not limitation, medical sensor 204 may be a temperature sensor disposed within medical device 102. Thus patient 100 may wear a badge, such as medical device 102, which dynamically displays the patient's temperature as a barcode. Any suitable dynamic medical data may be so displayed. The inner construction of medical device 102 includes a processor for processing the dynamic medical data so received.

In the embodiment depicted in FIG. 2, digital display 104 is further comprised of digital picture 208, which is optional. In the embodiment depicted in FIG. 2, digital picture 208 is a digital picture of patient 100 (see FIG. 1).

Figure 3:
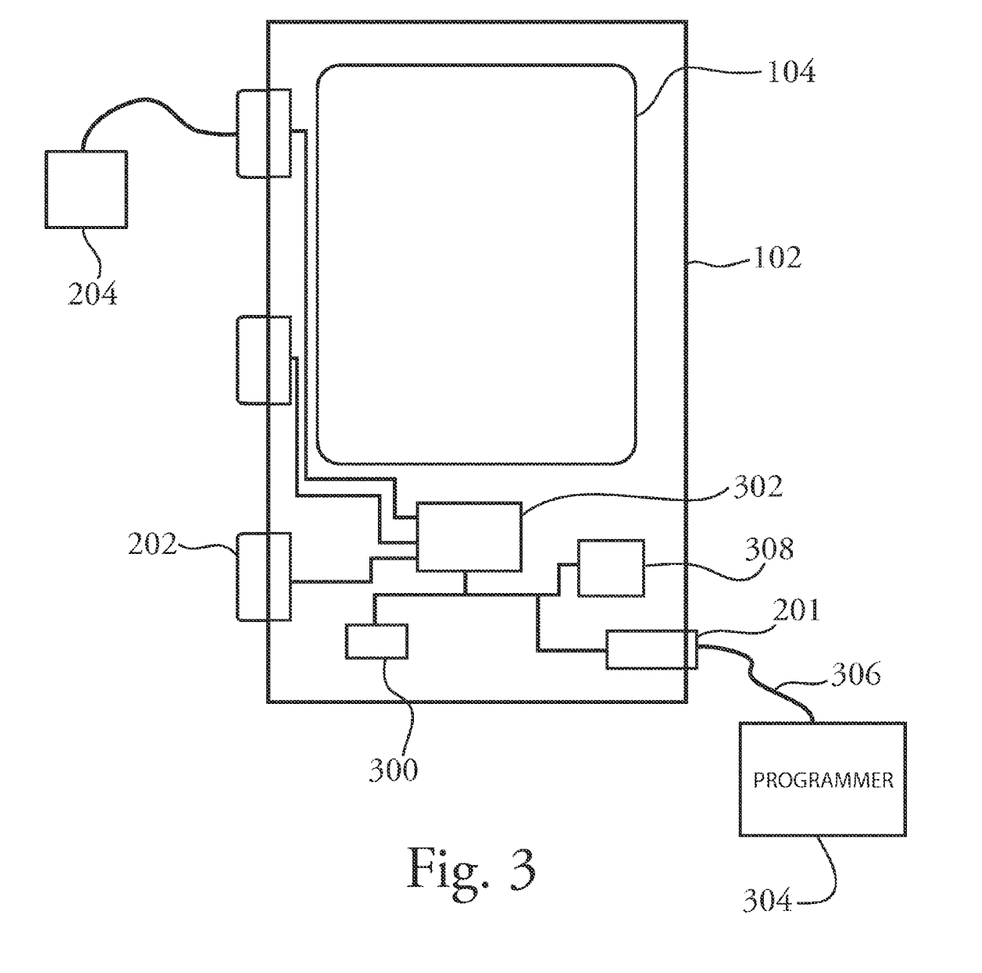
FIG. 3 is a schematic depiction of the inner connections of the medical device of FIG. 2.

FIG. 3 is a depiction of the inner construction of medical device 102 after the outer casing has been removed. Medical device 102 is comprised of a printed circuit board 300, processor 302 and data storage device 308. Board 300 causes the various input terminals (such as 201 and 202) to be in electrical communication with processor 302. Also illustrated in FIG. 3 is programmer 304 that is connected to programming input terminal 201 via line 306. In this manner, programming instructions can be sent to processor 302. In one embodiment, this permits the user to properly configure the processor 302 to receive and interpret the dynamic medical data received from medical sensor 204. In another embodiment, such programming instructions are sent to processor 302 through user input terminal 200 (see FIG. 2). Such programming instructions include, in one embodiment, a predetermined frequency of data queries to be performed. In one embodiment, the predetermined frequency is at least about once per five minutes. In such an embodiment, at least once per five minutes the processor 302 queries medical sensor 204 for the current value of the dynamic medical data. In another embodiment, such programming instructions include conditions necessary to trigger an alarm. Processor 302 processes the dynamic medical data so obtained into dynamic barcode data that is suitable for displaying on digital display 104. In one embodiment, such dynamic barcode data is stored in data storage device 308. The dynamic barcode data so stored can be displayed on digital display 104 in a variety of configurations.

Figure 4:
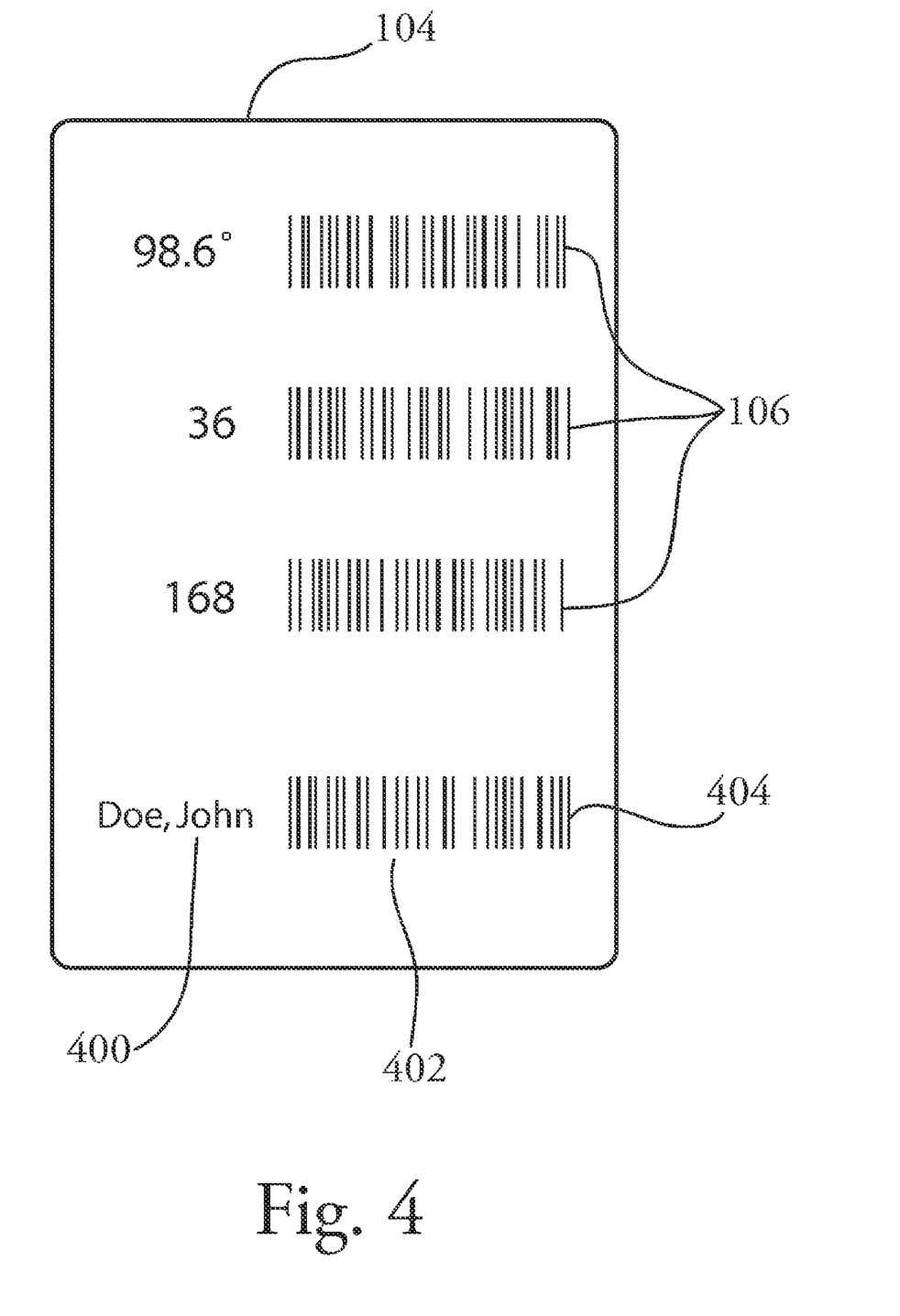
FIG. 4 is a depiction of one display configuration of the present invention.

FIG. 4 is a depiction of one configuration of digital display 104. In the embodiment depicted in FIG. 4, data is provided in both human readable format 400 and computer readable (e.g. barcode) format 402. In another embodiment, not shown, data is presented only in computer readable format, but is not displayed in human readable format. Such data may be dynamic barcode data 106 or static barcode data 404. As used in this specification, the term dynamic data refers generally to data that changes, or may change, at least about once over a period of about five minutes. Reference may be had to the use of the term "dynamic" as used and claimed in U.S. Pat. No. 6,082,620. Examples of such dynamic data include blood pressure, heart rate, temperature, blood oxygen level, and the like. Another example of dynamic data is a trend over time, e.g., average increase or decrease in heart rate over 12 hours. As used in this specification, the term static data refers to data which is not dynamic. More particularly, the term refers to data that does not change, or is unlikely to change, over a relatively short period of time. Examples of such static data include patient name, age, gender, address, insurance information, etc. Other examples of static data include medical information such as blood type, medications (including dosage, etc.) allergies, and other medical background information. Even further examples of static data include interactions and clinical encounters, including the names of treating medical providers.

In the embodiment depicted in FIG. 4, there is one barcode for each piece of data—either static or dynamic. In another embodiment, a single barcode (which is dynamic) encodes for one or more pieces of static and/or dynamic data. The transmission of complex information in a barcode is known in the art. Reference may be had, for example, to U.S. Pat. No. 6,666,377, the content of which is hereby incorporated by reference into this specification. In another embodiment, the barcode contains a pointer (i.e. primary key) that points to the location of an associated record in a database. Such a database may be stored, for example, in storage device 308 or on another (external) computer. Other suitable techniques for transmitting or associating data with the instant record would become apparent to one skilled in the art after benefiting from reading this disclosure. Such techniques are considered within the scope of the present invention.

Figure 5:
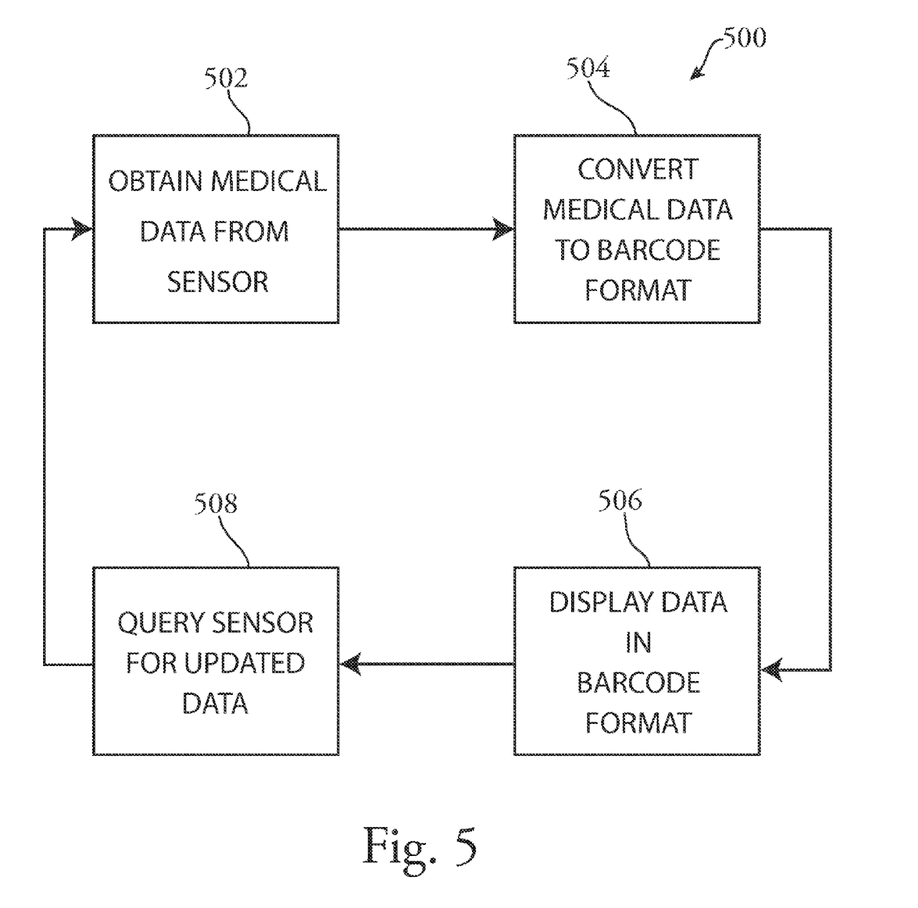
FIG. 5 is a flow diagram of one process for displaying a dynamic barcode.

FIG. 5 is a depiction of process 500 for use with the present invention. In the embodiment depicted, a medical device (such as device 102 of FIG. 1) is connected to a medical sensor which, in turn, is connected to a patient. In step 502 dynamic medical data about the patient is obtained by the medical sensor. For example, when the medical sensor is a temperature sensor, a certain voltage reading is transmitted from the temperature sensor to the medical device. In step 504, this dynamic medical data (the current voltage reading) is converted into barcode format. Thus, for example, the medical device applies a mathematical algorithm that converts the current voltage reading to a temperature value (such as an analog to digital converter (ACD) circuit), and thereafter converts the resulting temperature value to barcode format. In one embodiment, such a conversion includes the application of an encryption algorithm that encodes the data. As used in this specification, the term "encrypt" is given the same meaning as in U.S. Pat. No. 7,124,939 to Calaway, et al. (Method and Apparatus for Creating a Barcode), the content of which is hereby incorporated by reference into this specification.

Referring again to FIG. 5, in step 506, the resulting barcode format is converted into a displayed barcode that is graphically presented on a display located on the medical device. The displayed barcode remains on display until an updated barcode is generated. During step 508, the medical device queries the sensor for updated data. Upon receiving a query, the medical sensor provides the current dynamic medical data. Thus, a new dynamic medical data point is provided (i.e. step 502 is repeated) and the cycle begins anew. At any point after the first execution of step 506, a user can read the displayed barcode with a barcode scanner and obtain the most recent dynamic data.

Figure 6:
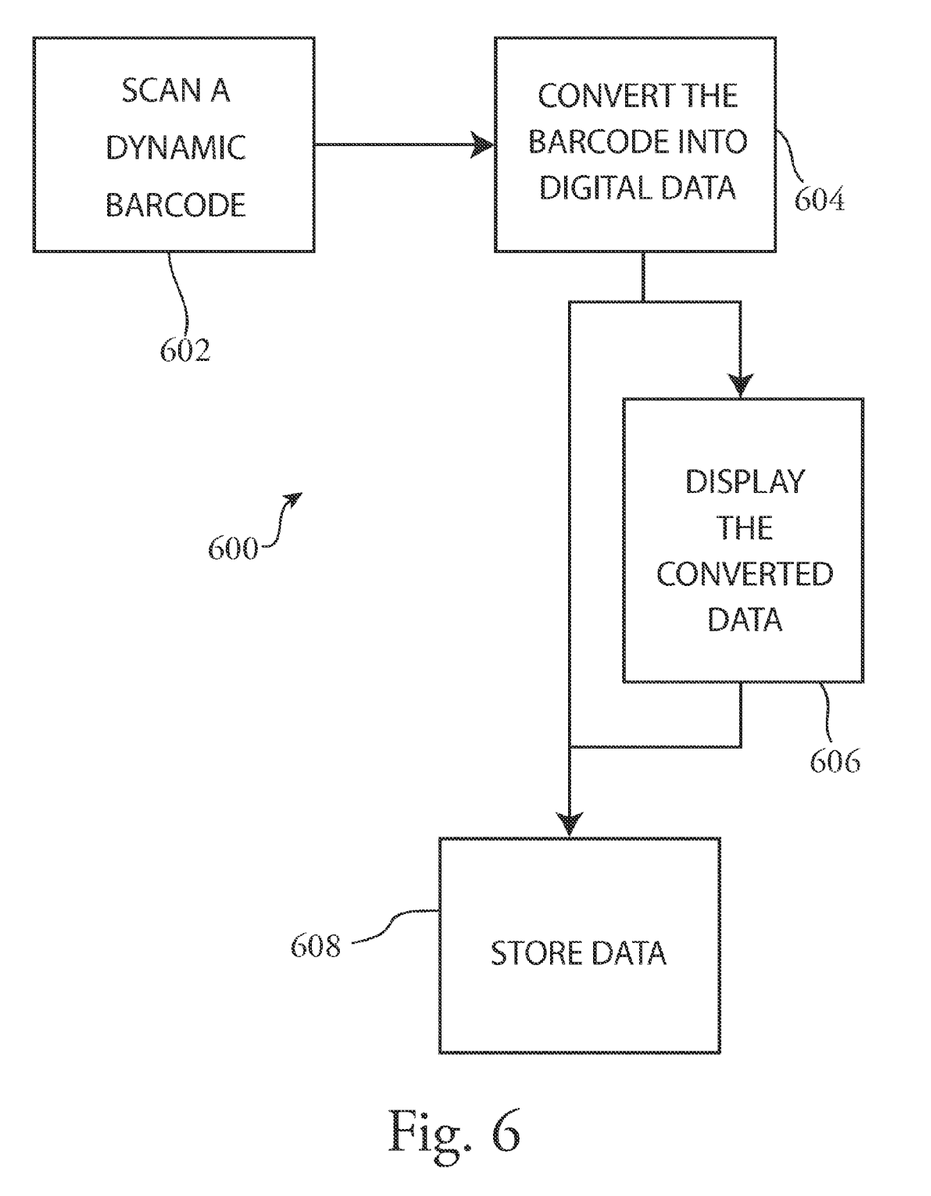
FIG. 6 is a flow diagram of another process for reading a dynamic barcode.

FIG. 6 is a depiction of process 600 wherein the displayed barcode is read. In process 600, medical practitioner approaches a patient that is connected to a medical device and sensor as previously discussed. The medical device includes a display is comprised of the dynamic barcode that represents the dynamic data obtained by the sensor. In one embodiment, the data is presented only in barcode format, such that the general public cannot read the medical data without a suitable barcode scanner.

In step 602 of process 600 (see FIG. 6), the displayed barcode is read with a barcode scanner by passing the scanner over the barcode. In some embodiments, the scanner is especially configured to read the displayed barcode. For example, for those embodiments where an encryption algorithm was applied to generate the dynamic barcode, the scanner is equipped with a de-encryption algorithm that permits the scanner to read the underlying dynamic medical data. In some embodiments, the barcode contains a prefix code that includes a password or similar prefix code. The barcode scanner detects the presence of such a prefix code and prompts the user to input the corresponding password or key. The underlying data is not displayed unless the correct password is entered. The barcode so read contains, in some embodiments, static identifying information about the patient. For example, the barcode may contain the patient's name or other identifying number. In another embodiment, two or more separate barcodes are read—one of which contains the aforementioned static data.

Referring again to FIG. 6, regardless of whether or not the barcode is an encrypted barcode or contains identifying information, the data read from the scanner in step 602 is converted into digital data in step 604. For example, if the sensor is a temperature sensor then the precise temperature that the barcode represents (e.g. 98° F.) is converted from barcode format to digital format in step 604. In step 606, which is optional, the resulting data is displayed. In some embodiments, the user of the data is not privy to the underlying medical data and simply scans the barcode (step 602) which converts the barcode into digital data (604) and stores the digital data (step 608) for later retrieval by a user who is privy to such medical information. In some embodiments, the data is not stored (i.e. step 608 is optional) and the data is merely viewed by the user of the scanner. In this manner, an unauthorized user can gather confidential medical data about one or more patients, without the confidence of the patients being violated by the unauthorized user.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A medical device system for displaying medical data concerning a patient comprising:
    a medical sensor that obtains dynamic medical data from a patient, wherein the dynamic medical data is displayed in a format that is both computer readable and not human readable;
    a data input terminal for connecting to said medical sensor and receiving said dynamic medical data therefrom;
    a processor for processing said dynamic medical data into dynamic barcode data; and
    a digital display and displayed on said digital display, a dynamic barcode, wherein:
        said dynamic barcode comprises said dynamic barcode data, and
        said dynamic barcode updates in response to said dynamic medical data received from said medical sensor through said data input terminal, and said dynamic medical data is displayed in a computer readable and non human readable format on said digital display;
    a scanner for scanning said dynamic barcode as scanned data;
    a data storage device for storing said scanned data, wherein said scanned data can only be accessed by providing a password.

2. The medical device as recited in claim 1, wherein said digital display consists of said dynamic barcode and said dynamic barcode data is not human readable.

3. The medical device as recited in claim 1, wherein a digital picture of the patient is displayed on said digital display.

4. The medical device as recited in claim 1, wherein said processor queries said medical sensor at predetermined intervals and updates said dynamic barcode at said predetermined intervals.

5. The medical device as recited in claim 1, wherein the data storage device stores both static data and said dynamic data.

6. The medical device as recited in claim 5, wherein said static data is displayed on said digital display within a static barcode.

7. The medical device as recited in claim 5, wherein said static data is displayed on said digital display within said dynamic barcode.

8. The medical device as recited in claim 5, wherein said static data includes identifying information about said patient.

9. The medical device as recited in claim 8, wherein said static data includes static medical information about said patient.

10. The medical device as recited in claim 9, wherein said dynamic barcode is encrypted.

11. The medical device as recited in claim 1, wherein said medical sensor is selected from the group consisting of a blood pressure sensor, a temperature sensor, a blood oxygen level sensor, a respiration rate sensor, a heart sensor, and combinations thereof.

12. The medical device system as recited in claim 1, further comprising an alarm operatively connected to said processor such that said alarm is triggered when said dynamic medical data meets a predetermined condition that is programmed into said processor.

13. A process for displaying dynamic patient medical data with a dynamic barcode comprising the steps of:
    obtaining dynamic medical data about a patient from a medical sensor wherein said dynamic medical data is not displayed in human readable format;
    convening said dynamic medical data to dynamic barcode data;
    displaying said dynamic barcode data on a digital display using a dynamic barcode while maintaining the confidentiality of the dynamic medical data by not displaying the data in human-readable format;
    querying said medical sensor at a predetermined interval and obtaining updated dynamic medical data from said medical sensor; and
    updating said dynamic barcode in response to said updated dynamic medical data;
    scanning said dynamic barcode by an individual, wherein said individual is not privy to said dynamic medical data.

14. The process as recited in claim 13, wherein said dynamic barcode is further comprised of static data.

15. The process as recited in claim 14, wherein said static data is comprised of identifying information about said patient.

16. The process as recited in claim 15, wherein said dynamic barcode data is encrypted.

17. The process as recited in claim 13, wherein said dynamic barcode data is not presented in human readable format.

18. A medical device for displaying medical data concerning a patient comprising:
    a first medical sensor for sensing a first dynamic medical data signal of a patient, wherein said dynamic medical data is not displayed in human readable format;
    a data input terminal for connecting to said first medical sensor and receiving said first dynamic medical data signal;
    a processor for processing said first dynamic medical data signal into a first dynamic barcode data; and
    a digital display and displayed on said digital display, a dynamic barcode, wherein:
        said dynamic barcode comprises said first dynamic barcode data, and
        said first dynamic barcode updates in response to said first dynamic medical data signal received from said first medical sensor through said data input terminal, and said dynamic medical data is displayed only in computer readable format.

19. The medical device as recited in claim 18, further comprising an alarm operatively connected to said processor such that said alarm is triggered when said dynamic medical data meets a predetermined condition that is programmed into said processor.

20. The medical device as recited in claim 18, further comprising a second medical sensor for sensing a second dynamic medical data signal of said patient, wherein:

said processor processes said second dynamic medical data signal into dynamic barcode data, and     said dynamic barcode comprises said second dynamic barcode data.

21. The medical device as recited in claim 18, further comprising a second medical sensor for sensing a second dynamic medical data signal of said patient wherein:

said processor processes said second dynamic medical data signal into dynamic barcode data;

said digital display is comprised of a second dynamic barcode; and     said second dynamic barcode comprises said second dynamic barcode data.

\* \* \* \* \*